(12) United States Patent
Walker

(10) Patent No.: US 6,264,697 B1
(45) Date of Patent: Jul. 24, 2001

(54) KNEE PROSTHESIS HAVING GUIDE SURFACES FOR CONTROL OF ANTERIOR-POSTERIOR DISPLACEMENT

(76) Inventor: Peter Stanley Walker, 13 Pembroke Rd., Northwood, Middlesex HA6 2HP (GB)

( * ) Notice: Subject to any disclaimer, the term of this patent is extended or adjusted under 35 U.S.C. 154(b) by 0 days.

(21) Appl. No.: 09/402,937
(22) PCT Filed: Apr. 15, 1998
(86) PCT No.: PCT/GB98/01098
§ 371 Date: Oct. 14, 1999
§ 102(e) Date: Oct. 14, 1999
(87) PCT Pub. No.: WO98/46171
PCT Pub. Date: Oct. 22, 1998

(30) Foreign Application Priority Data

Apr. 16, 1997 (GB) .................................................. 9707717

(51) Int. Cl.[7] ...................................................... A61F 2/38
(52) U.S. Cl. ................................. 623/20.27; 623/20.21; 623/20.14
(58) Field of Search ............................. 623/20.27, 20.18, 623/20.26, 20.14, 20.11, 20.24, 18.11, 16.11, 20.21

(56) References Cited

U.S. PATENT DOCUMENTS

| | | | |
|---|---|---|---|
| 4,209,861 | 7/1980 | Walker et al. | 3/1.911 |
| 4,216,549 | * 8/1980 | Hilberry et al. | 623/20.14 |
| 4,959,071 | * 9/1990 | Brown et al. | 623/20.27 |
| 5,011,496 | * 4/1991 | Forte et al. | 623/20.27 |
| 5,147,405 | 9/1992 | Van Zile et al. | 623/20 |
| 5,282,869 | * 2/1994 | Miyajima et al. | 623/20.27 |
| 5,330,532 | * 7/1994 | Ranawat | 623/20.27 |

FOREIGN PATENT DOCUMENTS

| | | |
|---|---|---|
| 0 627 203 | 12/1994 | (EP) . |
| 96/03097 | 2/1996 | (WO) . |

* cited by examiner

Primary Examiner—Pedro Philogene
(74) Attorney, Agent, or Firm—Burns, Doane, Swecker & Mathis, L.L.P.

(57) ABSTRACT

A condylar total knee replacement prosthesis is disclosed having interacting guide surfaces for control of anterior-posterior displacement. The prosthesis comprises a femoral component (1) having a pair of condylar surfaces (2,3), a tibial component having a tibial platform (4) and a bearing component interposed between the femoral and tibial components. A femoral guide surface (5) is located between the condyles and engages with a tibial guide surface (8) to cause the femoral component to displace posteriorly during flexing movements and displace anteriorly during extending movements. The femoral guide surface is offset posteriorly and downwardly from the center of major curvature of the femoral condyles.

9 Claims, 13 Drawing Sheets

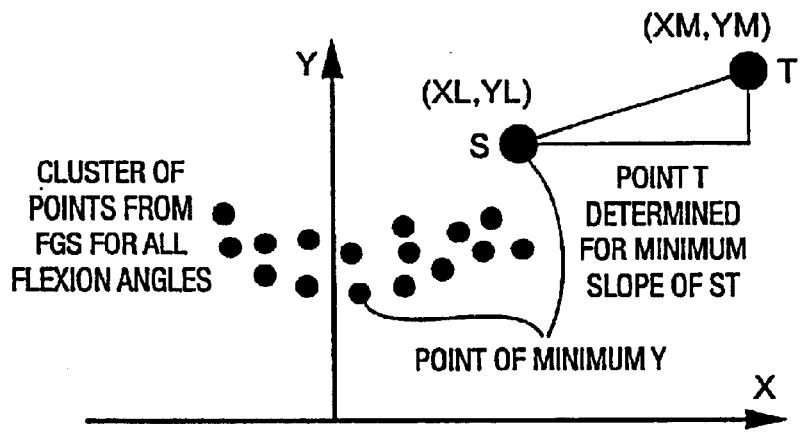
SYNTHESIS OF THE TIBIAL GUIDE SURFACE (TGS) FROM THE ACCUMULATION OF POINTS OF THE FEMORAL GUIDE SURFACE (FGS) AS THE FEMUR MOVES FROM ZERO TO MAXIMUM FLEXION
Fig.2
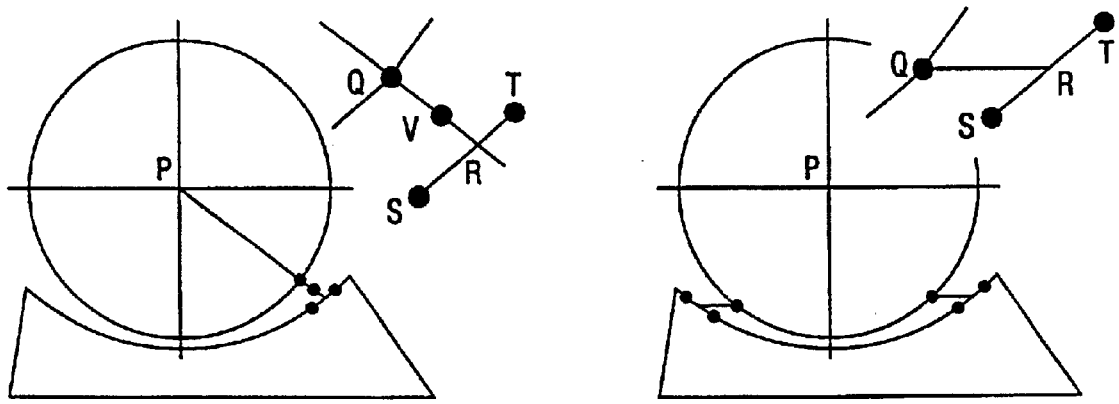
MODIFICATION OF THE FGS TO REDUCE LAXITY.
Fig.3
DETERMINATION OF THE LAXITIES IN THE ANTERIOR AND POSTERIOR DIRECTIONS.
Fig.4

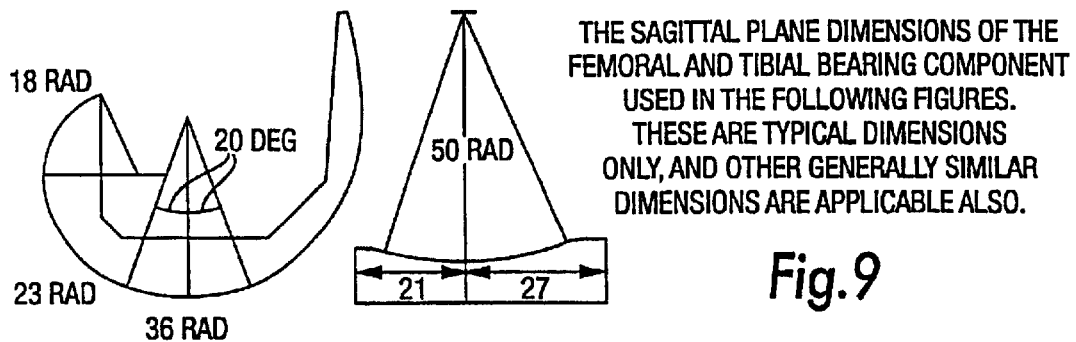

THE SAGITTAL PLANE DIMENSIONS OF THE FEMORAL AND TIBIAL BEARING COMPONENT USED IN THE FOLLOWING FIGURES. THESE ARE TYPICAL DIMENSIONS ONLY, AND OTHER GENERALLY SIMILAR DIMENSIONS ARE APPLICABLE ALSO.

Fig. 9

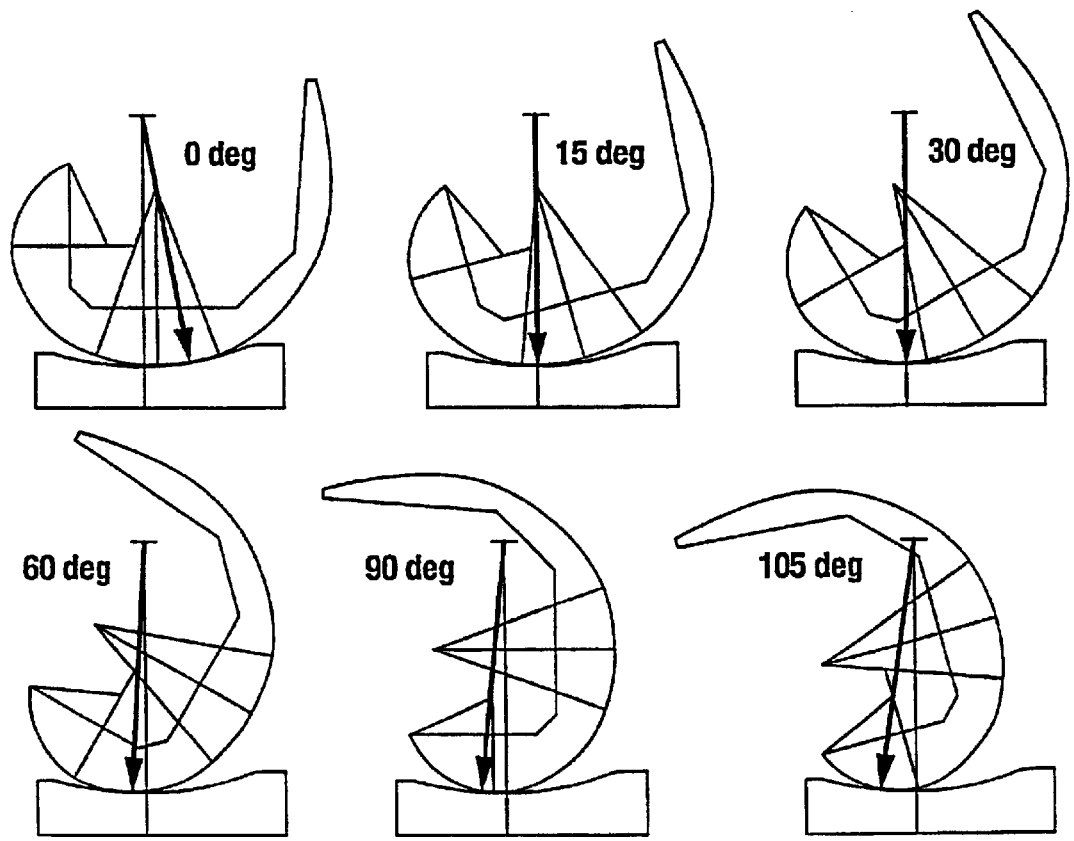

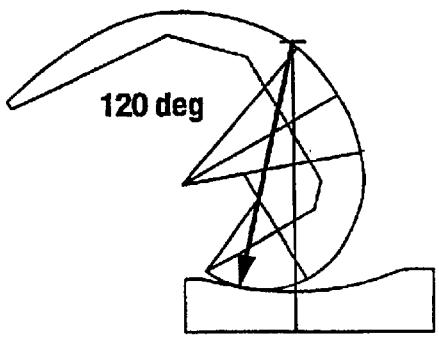

THE GENERAL PATTERN OF THE LOCATIONS OF THE CONTACT POINTS (INDICATED BY ARROWS) DURING FLEXION FROM 0 DEG TO 120 DEG. IN EXTENSION THE CONTACT IS ANTERIOR OF THE BOTTOM OF THE TIBIAL DISH. AT 15 DEG AND 30 DEG THE CONTACT IS AT THE BOTTOM OF THE DISH. FROM 60 DEG TO 120 DEG THERE IS A POSTERIOR DISPLACEMENT, MORE RAPIDLY AS FLEXION PROCEEDS.

Fig. 10

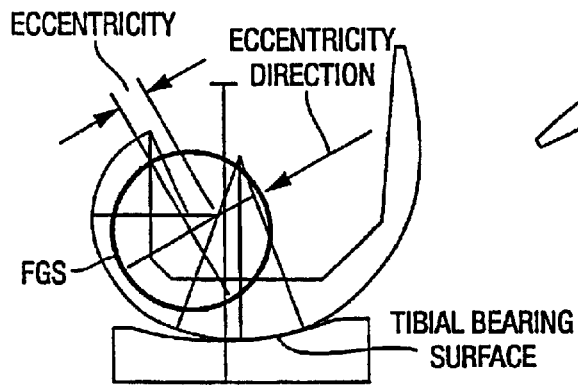

THE INITIAL FGS IS DEFINED AS A CIRCLE
WITH ECCENTRICITY ANGLE 30 DEG AND
ECCENTRICITY 5 MM (CAM OFFSET ANGLE 210°)

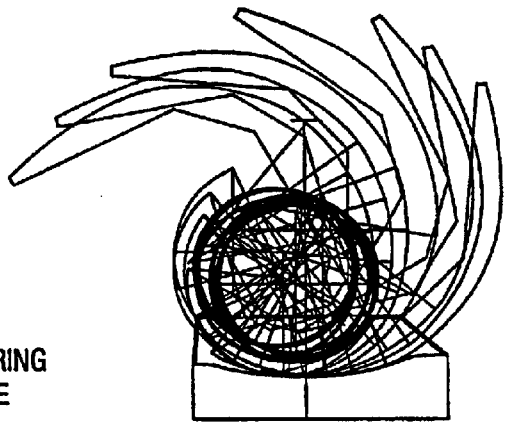

THE FEMORAL COMPONENT WITH ITS FGS
IS PLACED INTO THE REQUIRED SUCCESSIVE
POSITIONS ON THE TIBIAL BEARING SURFACE

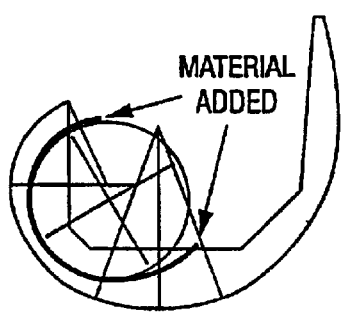

THE FGS IS THEN MODIFIED BY ADDING
MATERIAL ANTERIORLY AND POSTERIORLY

THE OUTER LOCUS OF THE FGS DEFINES
THE TGS, WITH THE ANTERIOR AND
POSTERIOR HEIGHTS SPECIFIED

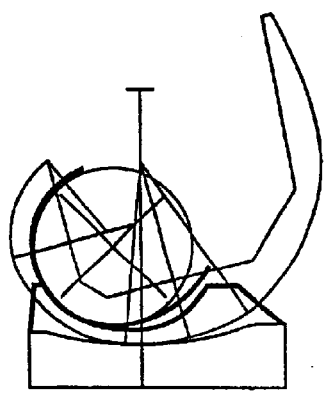
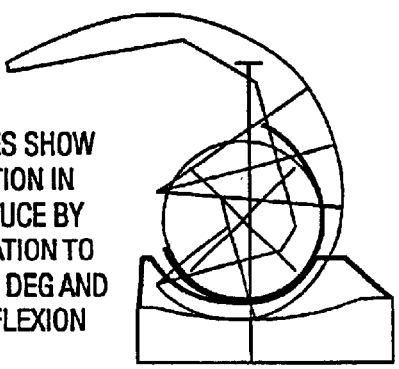

THESE FIGURES SHOW THE REDUCTION IN LAXITY PRODUCE BY THE MODIFICATION TO THE FGS, AT 15 DEG AND AT 115 DEG FLEXION

THE METHOD FOR GENERATING THE TGS FROM AN INITIAL FGS, ILLUSTRATED GRAPHICALLY

Fig. 11

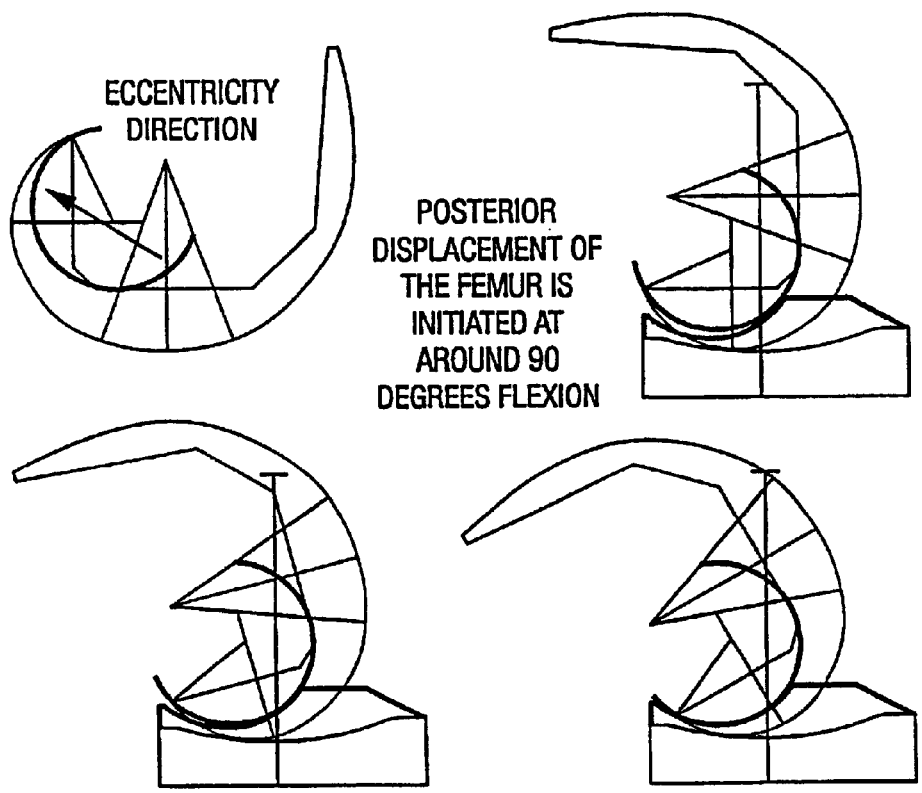

WHEN THE ECCENTRICITY DIRECTION IS ABOVE THE HORIZONTAL (ARROW), THE CONTACT POINTS ARE POSTERIORLY DISPLACED AFTER ABOUT 90 DEGREES FLEXION, AND THERE IS CONTROL OF ANTERIOR-POSTERIOR DISPLACEMENT. AT FLEXION ANGLES LESS THAN THIS, THERE IS NO CONTROL OF THE DISPLACEMENTS.

Fig. 13

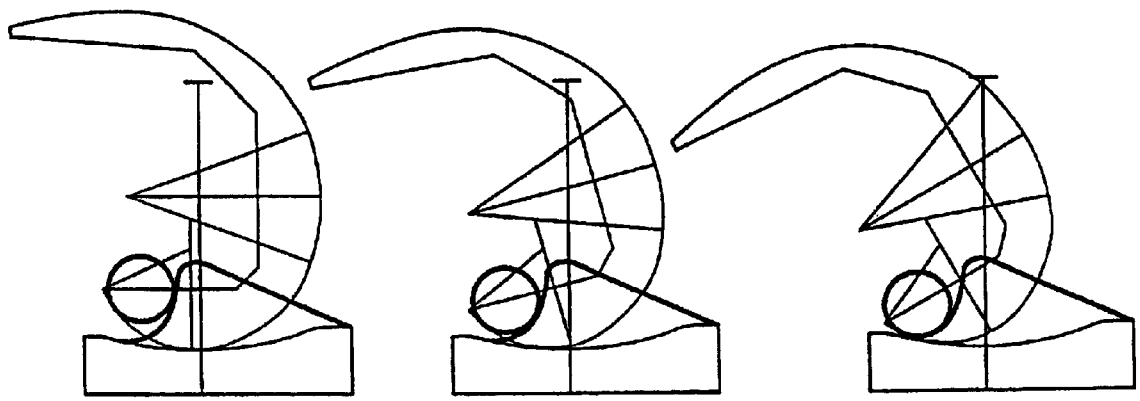

WHEN THE RADIUS OF THE FGS IS REDUCED AND THE ECCENTRICITY INCREASED, POSTERIOR DISPLACEMENT IS INDUCED AFTER AROUND 90 DEGREES FLEXION. THIS IS THE PRINCIPLE OF THE POSTERIOR STABILISED TYPE OF DESIGN.

Fig. 14

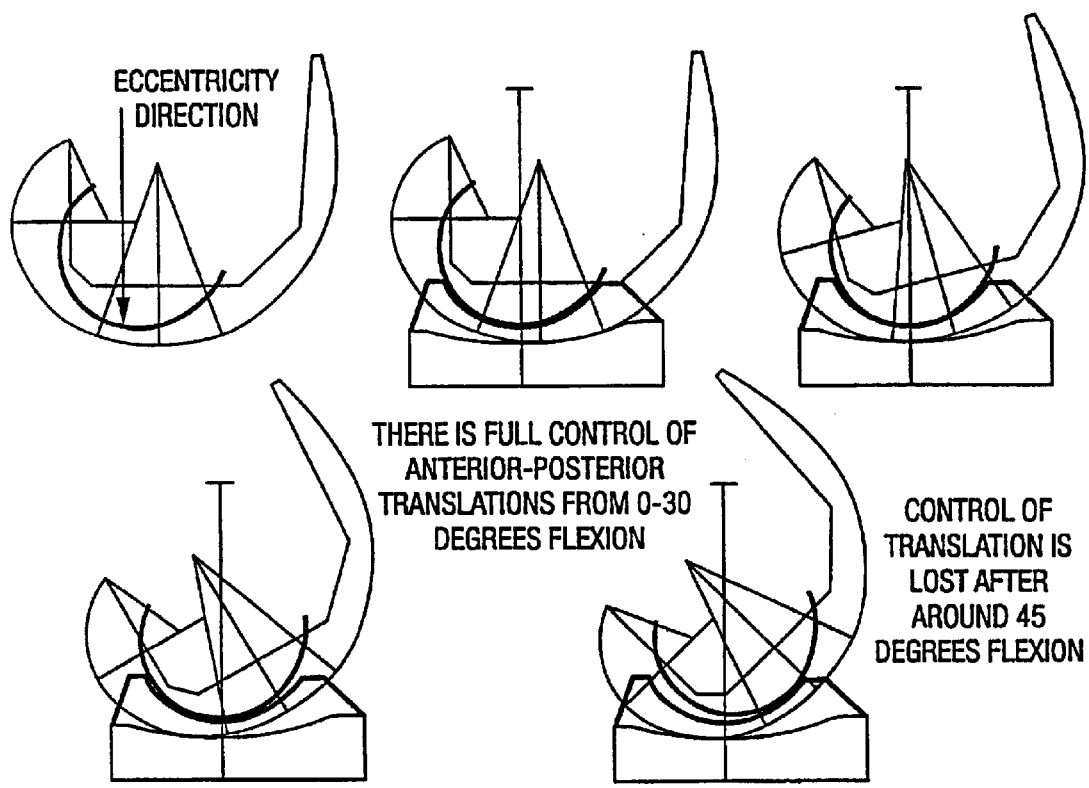

WHEN THE ECCENTRICITY ANGLE IS 90 DEGREES BELOW THE HORIZONTAL, THERE IS ANTERIOR TRANSLATION AS THE KNEE EXTENDS FROM 15 TO 0 DEGREES. THERE IS FULL CONTROL OF THE TRANSLATIONS UP TO AROUND 30 DEGREES FLEXION. AFTER AROUND 45 DEGREES THERE IS NO CONTROL OF THE TRANSLATIONS.

Fig. 15

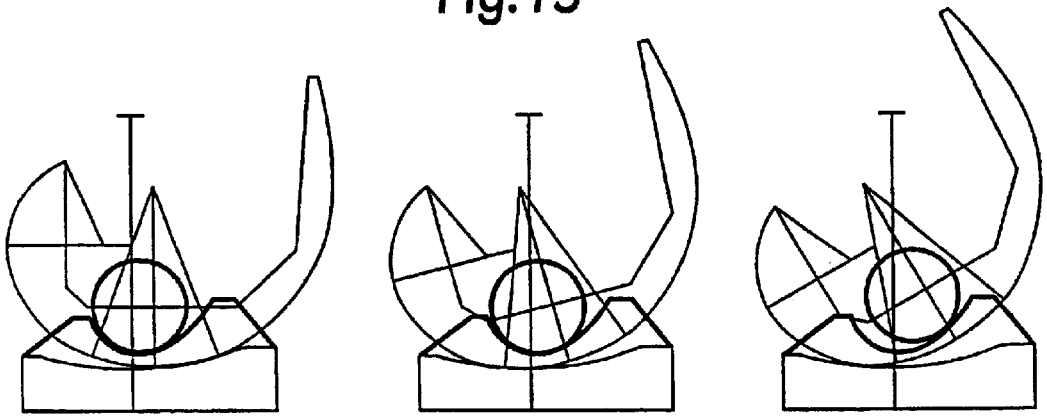

WHEN THE RADIUS OF THE FGS IS REDUCED AND THE ECCENTRICITY INCREASED, ANTERIOR-POSTERIOR TRANSLATION IS CONTROLLED IN THE FIRST 30 DEGREES OF FLEXION. ANTERIOR FEMORAL TRANSLATION IS CONTROLLED UP TO AROUND 45 DEGREES AFTER WHICH THERE IS NO CONTROL OF THE TRANSLATIONS.

Fig. 16

KNEE PROSTHESIS HAVING GUIDE SURFACES FOR CONTROL OF ANTERIOR-POSTERIOR DISPLACEMENT

BACKGROUND OF THE INVENTION

1. Field of the Invention

This invention relates to a total knee replacement prosthesis (TKR). Total knee replacement involves the surgical removal of the entire natural knee bearing surfaces and their replacement with artificial femoral and tibial components.

2. Description of Related Art

The invention is concerned with a type of TKR which includes femoral condylar surfaces which, to some extent, mimic the shape of the natural condyles and an interposed bearing component supported on a tibial platform. Condylar TKRs generally comprise (a) a femoral component having a pair of condylar surfaces, (b) a tibial component having a tibial platform fixed to the resected tibia, and (c) a bearing component usually of low friction plastic material interposed between the condylar surfaces and the tibial platform. The bearing component generally has dished surfaces for receiving the condylar surfaces of the femoral component. The bearing component can be made to be fixed onto the tibial platform or be rotatable and/or slidable in the anterior/posterior direction.

Stability of the artificial knee joint is provided by the dishing of the bearing surfaces and by the ligaments. In all cases, the collateral ligaments are required. In a fixed bearing design with dished bearing surfaces, the stability is sufficient particularly when there is a compressive force acting across the joint. In this situation, the cruciate ligaments are not necessary. For shallow bearing surfaces, which have the advantage of allowing extra freedom of motion, the posterior cruciate ligament is required. The above also applies to a mobile bearing design which only allows rotation. However, when anterior-posterior translation is allowed, the posterior cruciate ligament is required, no matter how dished are the bearing surfaces.

In the natural knee in extension, contact area is central on the tibial bearing surface or even anterior to the centre. As the knee is flexed, the contact area moves progressively posteriorly. This is important in that it provides an increasing lever arm to the quadriceps muscle in activities such as stair climbing and rising from a low chair, when there are high flexing moments acting on the knee. In addition, it is considered to be highly desirable for the femur to be displaced posteriorly with respect to the tibia at the higher flexion angles, since this will generally avoid posterior impingement of bone and soft tissues, allowing for a high range of flexion.

While proposals have been made in total knee design to provide for posterior displacement of the contact point with flexion, the corresponding problem of deliberately causing the contact point to be displaced anteriorly on extension, and the maintenance of stability during these movements has not been explored in prior proposals. The advantage of anterior displacement towards extension is an increase in lever arm of the hamstrings and gastrocnemius, thus helping to prevent hyperextension. It is, therefore, to a solution of these problems that the present inventions directed.

OBJECT AND SUMMARY

It is, therefore, an object of the present invention to provide a TKR in which the femoral component provides for roll-back posteriorly with flexion and for a corresponding compensatory displacement anteriorly with extension, while maintaining stability of the joint during such movements.

According to one aspect of the present invention there is provided a total knee replacement prosthesis which comprises:

(a) a femoral component having a pair of condylar surfaces (b) a tibial component adapted to be attached to the tibia and having a tibial platform fixed to the resected tibia, (c) a mobile bearing component which is interposed between each condylar surface and the tibial platform and which has dished bearing surfaces adapted to support and conform with the corresponding femoral condylar surfaces, the mobile bearing component being slidable on the tibial platform in the anterior/posterior direction; said femoral component having an intercondylar guide surface which is adapted to engage a corresponding tibial guide surface which is fixed on the tibial platform or is integral therewith, the intercondylar surface being round and having a center of curvature when viewed sagittally, which is offset from a major center of curvature of the femoral condylar surfaces.

Displacement of the femoral component with respect to the tibial component can be effected by 'rigid' body motion or by 'contact' point motion or by a combination of both. In rigid body motion, the femoral component moves bodily with respect to a tibial platform which is fixed to the tibia. Such movement can be effected by permitting a tibial bearing component to be mobile on the tibial platform. On the other hand, the contact point (or centre point of a contact area) between the femoral-tibial bearing surfaces as viewed in a sagittal plane moves during flexion. These relative movements will be discussed in more detail subsequently in this specification in connection with various figures of the drawings. In most cases, there will be a mixture of rigid body and contact point motions.

Preferably, the tibial guide surface has an anterior and posterior upward sweep which engages in recesses in the femoral component to contributive to the stability of the prosthesis at or close to maximum flexion and extension, while anterior-posterior stability is also afforded during the mid-range of flexion due to similar engagements. The tibial guide surface may also include lateral surfaces which engage with corresponding lateral surfaces adjacent to the condylar surfaces of the femoral component.

In one embodiment, the tibial guide surface may be an integral part of the tibial platform, or alternatively be a plastic component fixed relatively to the anterior/posterior direction on the tibial platform. The guide surface may be rotatably mounted on the tibial platform in order to provide internal/external rotation of the knee joint to a desirable degree, e.g. ±12 to 15 degrees. This kind of arrangement is illustrated in FIGS. 1A and 1B. Alternatively, the guide surface may be fixed relatively to the tibial platform and the tibial component mounted for rotation within or on a member fixed to the resected tibia. For example, the tibial component may incorporate a stem which is rotatbly received within a tubular member fixed into the tibial bone canal.

In cases where the tibial guide surface is a part of or fixed in the anterior/posterior direction to the tibial platform, the bearing component may take the form of two plastic bearing components each moveable within limits on the tibial platform. In this case, the bearing components may be guided on the tibial platform in such a way as to leave clearance between the tibial guide surface and the bearing components, to permit combinations of rotational and anterior/posterior movements. Again, this is illustrated in FIG. 1A.

In an alternative embodiment of the invention the tibial guide surface is an integral part of the bearing component. This is illustrated in FIG. 17. In this case, the bearing component can be fixed to the tibial platform. Sufficient laxity is then required between the femoral and tibial bearing surfaces to allow both rotational and anterior/posterior (A-P) motions to occur. If the bearing component is allowed to rotate about a vertical axis in the tibial platform, femoral-tibial laxity is only required to accommodate the A-P translation.

Posterior displacement of the femoral-tibial contact point is achieved in accordance with the invention by providing a rounded femoral guide surface, (typically as an intercondylar femoral guide surface), having a centre of curvature, when viewed sagittally, which is offset from a major centre of curvature of the femoral condylar surfaces.

By 'major centre of curvature' in this context is meant the centre of the major part of the arc from the lowest point (at 0° flexion) of the femoral condylar surface to its posterior-most point.

A degree of posterior displacement of the contact point from the maximum extension position to the maximum flexion position of between about 6 and 16 mm is aimed for. In a mobile bearing design, as shown in FIG. 1A, the motion of the contact point is the same as the rigid body motion of the femoral component. In a fixed bearing design where the tibial bearing surfaces are dished, as shown in FIG. 17, the contact point motion is more than the rigid body motion. The required anterior/posterior movement of the femoral component on the tibial guide surface is achieved by forming the tibial and/or femoral guide surfaces as cam surfaces so as to cause displacement of the femoral component in the anterior/posterior (A-P) direction with flexion or extension. The aim is to achieve a cam surface allowing only a small amount of A-P laxity or play, so as to control the A-P position throughout the entire range of flexion.

The method of achieving this by a series of iterative incremental angular movements of the component is described below with regard to the accompanying Figures and the invention also includes such method.

BRIEF DESCRIPTION OF THE DRAWINGS

In the accompanying drawings:

FIGS. 2, 3 and 4 illustrate the method of determining laxities of the embodiment shown in FIG. 1B;

FIG. 9 shows the radii at different portions of the femoral and tibial bearing components whose movements and interaction is illustrated in FIGS. 10 to 16;

FIG. 10 shows the change in the contact point or areas at different flexions;

FIG. 11 illustrates a method of generating the tibial guide surface (TGS) for a given femoral guide surface (FGS);

FIG. 13 illustrates the behaviour of a prosthesis where the eccentricity direction is above the horizontal (cam offset angle of less than 180°);

FIG. 14 illustrates the situation where the radius of the FGS is reduced and the eccentricity increased;

FIG. 15 illustrates the behaviour of a prosthesis having a cam offset angle of 270°;

FIG. 16 shows the effect of reducing the FGS radius and increasing the eccentricity;

DETAILED DESCRIPTION OF THE PREFERRED EMBODIMENTS

Figure 1A:
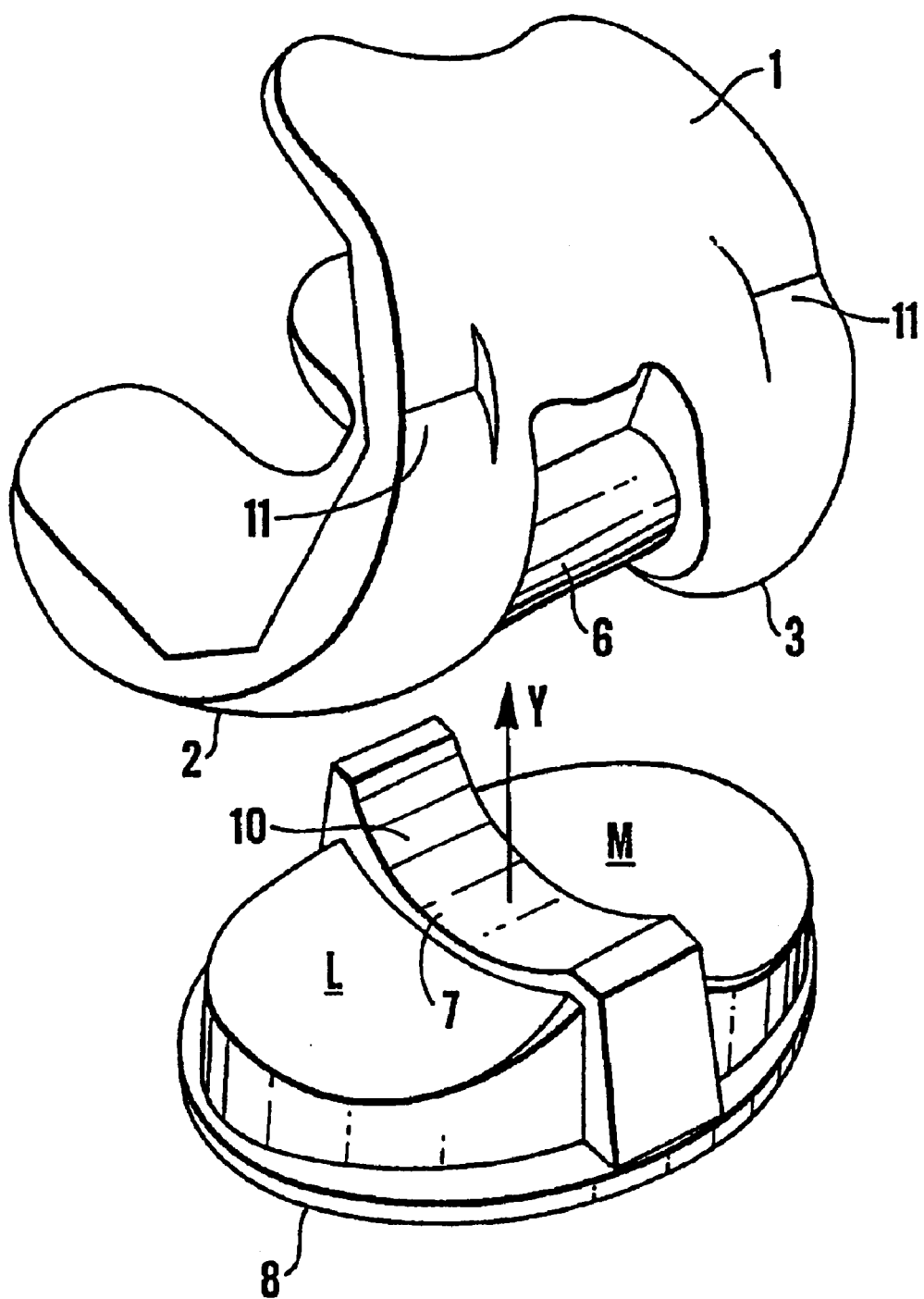
FIG. 1A is a perspective exploded view of a first embodiment in accordance with the invention.
Figure 1B:
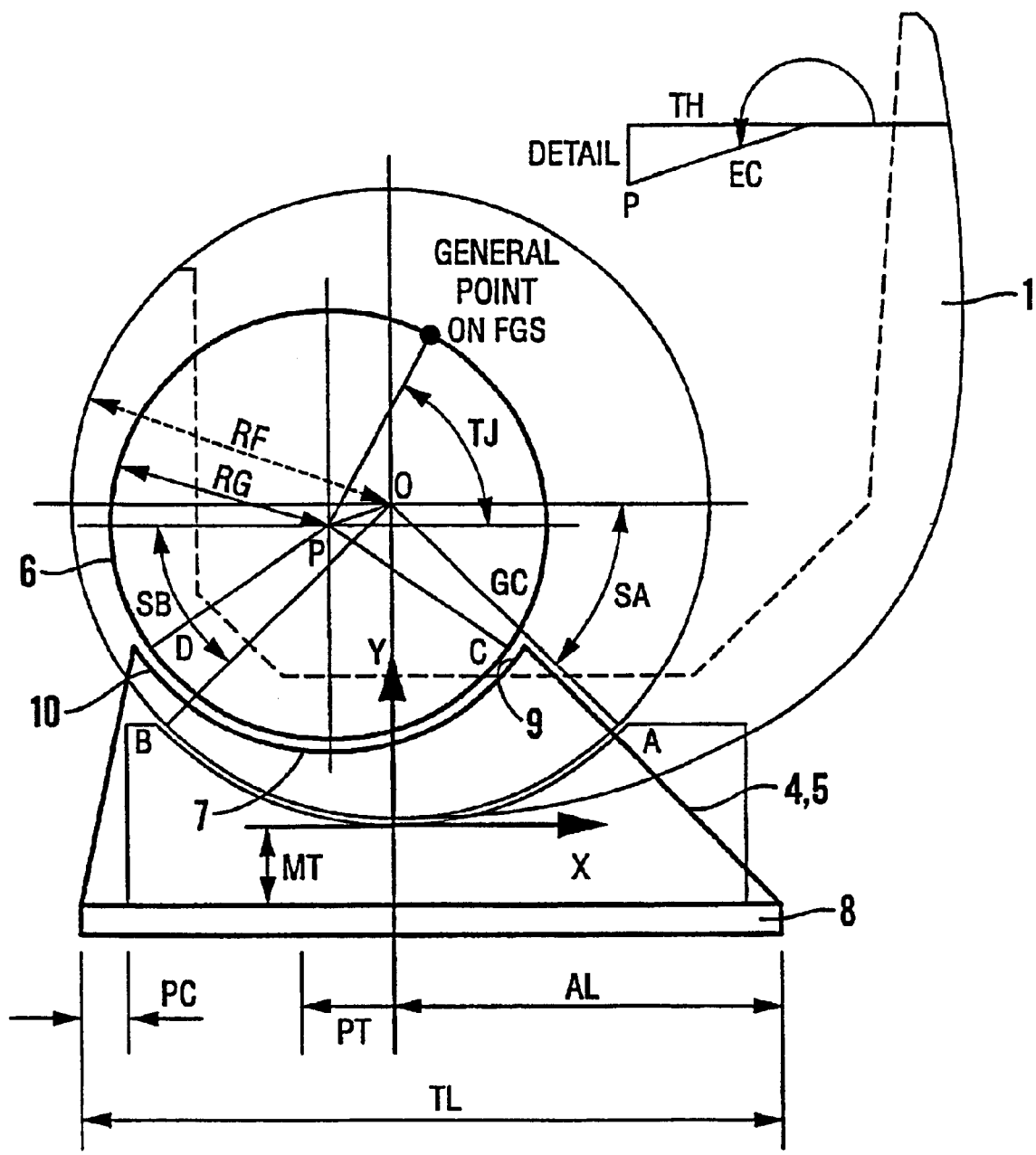
FIG. 1B is a sagittal view of the embodiment shown in FIG. 1.

The geometry at zero flexion for a mobile-bearing configuration is shown in FIG. 1B. The sagittal outline of a femoral component includes a posterior radius RF with centre O. Femoral component 1 with bearing surfaces 2 and 3 is supported on a mobile bearing component comprising two pairs 4 and 5. Radius RF of the mobile bearing is extended anteriorly to point A and posteriorly to a point B for a fully-conforming mobile-bearing design. The heights of A and B describing the arc of the dished surface of the plastic mobile bearing 4,5 are chosen to provide the required contact area and stability, which is quantified by the angles SA and SB. The plastic mobile bearing is shown with minimum thickness MT and a distance of AL from the anterior to the lowest point on the bearing. The bearing locates on a smooth metal plate of length TL. At zero flexion the bearing is chosen to locate close to the anterior of the plate and with a distance PC to the posterior of the plate.

The femoral component has an intercondylar notch in which is located a Femoral Guide Surface 6 (FGS) which engages with a tibial guide surface 7 (TGS). The FGS is convex, and the TGS is concave. The latter is fixed in an anterior/posterior direction with respect to a metal tibial plate 8, such that by its interaction with the Femoral Guide Surface (FGS), the femoral component can be made to translate relative to the tibia. The starting point for the shape of the FGS is a circular arc of radius RG and centre P which is offset from 0 by a distance EC at an angle of TH from the horizontal. As shown in the detail scrap view in FIG. 1B, TH is measured as shown from the horizontal so that an angle greater than 180° represents a centre of curvature P of the FGS which lies below the horizontal plane passing through the centre point O and posteriorly thereof. This is referred to subsequently in this specification as the cam offset angle. As the femur flexes from zero to maximum, it is required that the centre of the femoral component O displaces posteriorly by PT, moving continuously with flexion.

The initial problem is to synthesise the tibial guiding surface, which is depicted as a concave arc of unspecified shape. The heights of the TGS at the anterior and posterior are defined by a stability requirement when the FGS is pressing against the TGS at points C or D. If V is the vertical force across the knee and H is the AP shear force, stability is just achieved when angle GO is given by:

$$\tan(GO) = V/H \quad (1)$$

The requirement that posterior displacement is positive for all angular increments, is expressed at any flexion angle FLEX as:

$$d(PT)/D(FLEX) > 0 \quad (2)$$

For a total range of flexion FM, to satisfy equation (2):

$$(180-FM) > TH > 0 \quad (3)$$

This indicates that the line OP lies in the third quadrant. Hence, the largest Y-coordinate of point D is at zero flexion, and of point C is at maximum flexion FM. The Y coordinates of C and D are:

$$YC = RF - [EC \cdot \sin(TH+FM) + RG \cdot \sin(GA)] \quad (4)$$

$$YC = RF - [EC \cdot \sin(TH) + RG \cdot \sin(GA)] \quad (5)$$

For convenience the height of the anterior and posterior of the TGS are taken to be the largest of these values, denoted HT.

Discrete points are calculated around the FGS at small angular increments, TJ being any particular angle around the circle, with the femur at zero flexion:

$$XP(TJ,0) = RG \cdot \cos(TJ) - EC \cdot \cos(TH) \quad (6)$$

$$YP(TJ,0) = RF + RG \cdot \sin(TJ) - EC \cdot \sin(TH) \quad (7)$$

Points at zero flexion are stored with a Y value below HT, the maximum height of the TGS. The femur is then flexed through a small angle DF. The posterior displacement of femoral origin 0 is assumed to be linear with flexion. For a total displacement PT through the flexion range FM, the displacement through angle DF is:

$$PT(DF) = PT \cdot DF/FM \quad (8)$$

All of the points of the FGS are then transformed according to:

$$XP(TJ,DF) = XP(TJ,O) \cdot \sin(DF) + YP(TJ,O) \cdot \cos(DF) - PT(DF) \quad (9)$$

$$YP(TJ,DF) = XP(TJ,O) \cdot \cos(DF) - YP(TJ,O) \cdot \sin(DF) + RF \quad (10)$$

Again, points are stored with a Y value less than HT. This process is repeated until the maximum flexion angle FM.

At this stage a cluster of stored points is obtained. The initial TGS is given by the exterior locus of the points. To determine the points on this locus, the following algorithm is used (FIG. 2). The point with the minimum Y value is determined, (XL, YL). The next point in a positive X direction (XM, YM) is found by a searching routine satisfying:

$$XM > XL, \text{ and } (YM-YL)/(XM-XL) \text{ is a minimum} \quad (11)$$

This process is continued until no further points can be found. The same process is used to determine the points at X<XL. Ideally the points are connected with splines but for this analysis an approximation is mad with short line segments joining successive points, with minimal error.

It is found that at any flexion angle, when the FGS is superimposed on the TGS, there is an anterior and posterior space such that displacements could occur and there would not be a unique position of the femur on the tibia. This "laxity" can be reduced as follows. It can be visualised that an anterior region of the TGS could be formed as the posterior part of the FGS sweeps over at high flexion angles. It is possible therefore that this anterior region could be filled by an expanded anterior part of the FGS, which would move out of the TGS in early flexion. To examine this possibility, the femur is flexed from zero to FM in the same angular increments as before, and at each angle, each point Q on the FGS for YQ<HT is identified (FIG. 3).

The intersection of P0 with a line segment on the TGS is calculated, point R. RMAX is defined as the upper limit for the radius of the FGS based, for example, on the required dimensions for the pate linr groove. Point V is such that PV=RMAX. The coordinates of Q are changed according to:

$$\text{If } PR < RMAX, \; XQ = XR, \; YQ = YR \quad (12)$$

$$\text{If } PR < RMAX, \text{ and } PQ < PV, \; XQ = XV, \; YQ = YV \quad (13)$$

By carrying out this procedure it is found that the FGS is expanded in the leading and trailing regions, reducing the laxity. Further iterations for either the FGS or TGS do not result in any further changes.

The final laxity is calculated at each of the angular increments (FIG. 4). Again, each point on the FGS was examined for which YQ<HT. The intersection of a horizontal line through a line segment on the TGS is calculated, and the length OR calculated QR would be the anterior laxity of the femur if point Q was the first point to contact the TGS. The values of QR for all points on the FGS to the right of L are calculated. The minimum value is the relevant value of the anterior laxity.

The values of anterior and posterior laxity are then used as a criterion for determining the best design of the FGS and TGS. If AL (TH) and PL(TH) are the laxities at any flexion angle TH, the following criteria are considered:

$$\text{Minimise: } F1 = \sum_{O}^{FM} (AL(TH) + PL(TH)) \quad \text{criterion}(1)$$

This minimises the overall AP laxity throughout motion, but gives equal weight to a small number of large displacements or a large number of small displacements.

$$\text{Minimise: } F2 = \sum_{O}^{FM} (AL(TH))2 + (PL(TH)2) \quad \text{criterion}(2)$$

This is similar to criterion 1 but is biased against large laxities. Minimise the maximum value of F3=(AL(TH)+PL(TH) criterion (3) This is based entirely on the maximum total laxity at any angle. The dimensions and functional parameters for a typical condylar knee are taken to be:

Femoral radius RF=22 mm
Posterior displacement PT=6 mm
Stability angle of bearings SA=45°
Stability angle of TGS GA=35°
Maximum flexion angle FM=120°
Using equation (3) for the FGS angle:
60°≧TH≧0

The design problem is then stated as:
Determine the optimum design of the FGS and TGS, according to criterion 1, 2 or 3, for the above parameters for a condylar replacement knee, in the ranges:
60°≧TH≧0°(derived from equation 3) and 18 mm≧RG≧10 mm (geometrical considerations)

The FGC eccentricity value EC is not treated as a variable, as it is determined by the choice of the posterior displacement PT and the starting angle of the FGS, TH.

$$EC=PT/(\cos TH+\cos(TH+FM)) \quad (14)$$

The flexion range is taken to be 0- 120° (FM=120°) in increments of 30°. The points on the FGS are taken at 2" increments. These values are found to result in sufficient points on the TGS, with point spacing of less than 1 mm, to justify the approximation of short line segments for the TGS.

Results

Figure 5:
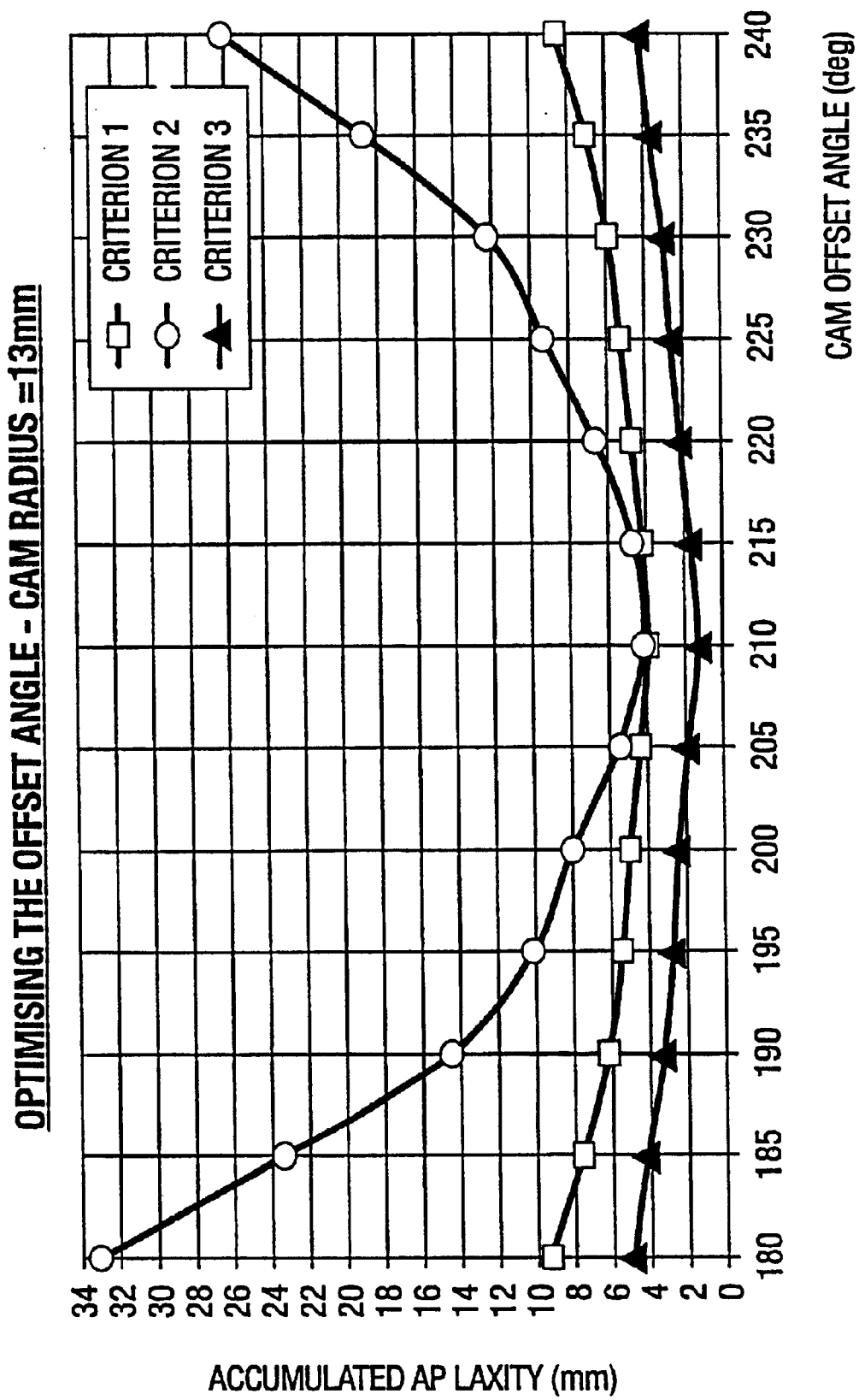
FIG. 5 shows graphically the accumulated anterior/posterior laxity at a number of cam offset angles.

Of the two parameters, the FGS cam offset angle TH, and the FGS cam radius RG, the former was the most influential. FIG. 5 shows the A-P laxity values for the three criteria. For criterion 1, the accumulated laxities for the 5 flexion positions 0, 30, 60, 90, 120) were the least at only 4 mm for a TH of 210°. The laxity increased to 10 mm at the extremes of TH. Criterion 2 gave the same minimum point at 210°, with exaggerated differences at the extremes due to the square function. Criterion 3 again gave TH=210° as the minimum, with a maximum laxity of only 1.3 mm as against 5 at the extremes of TH.

Figure 6:
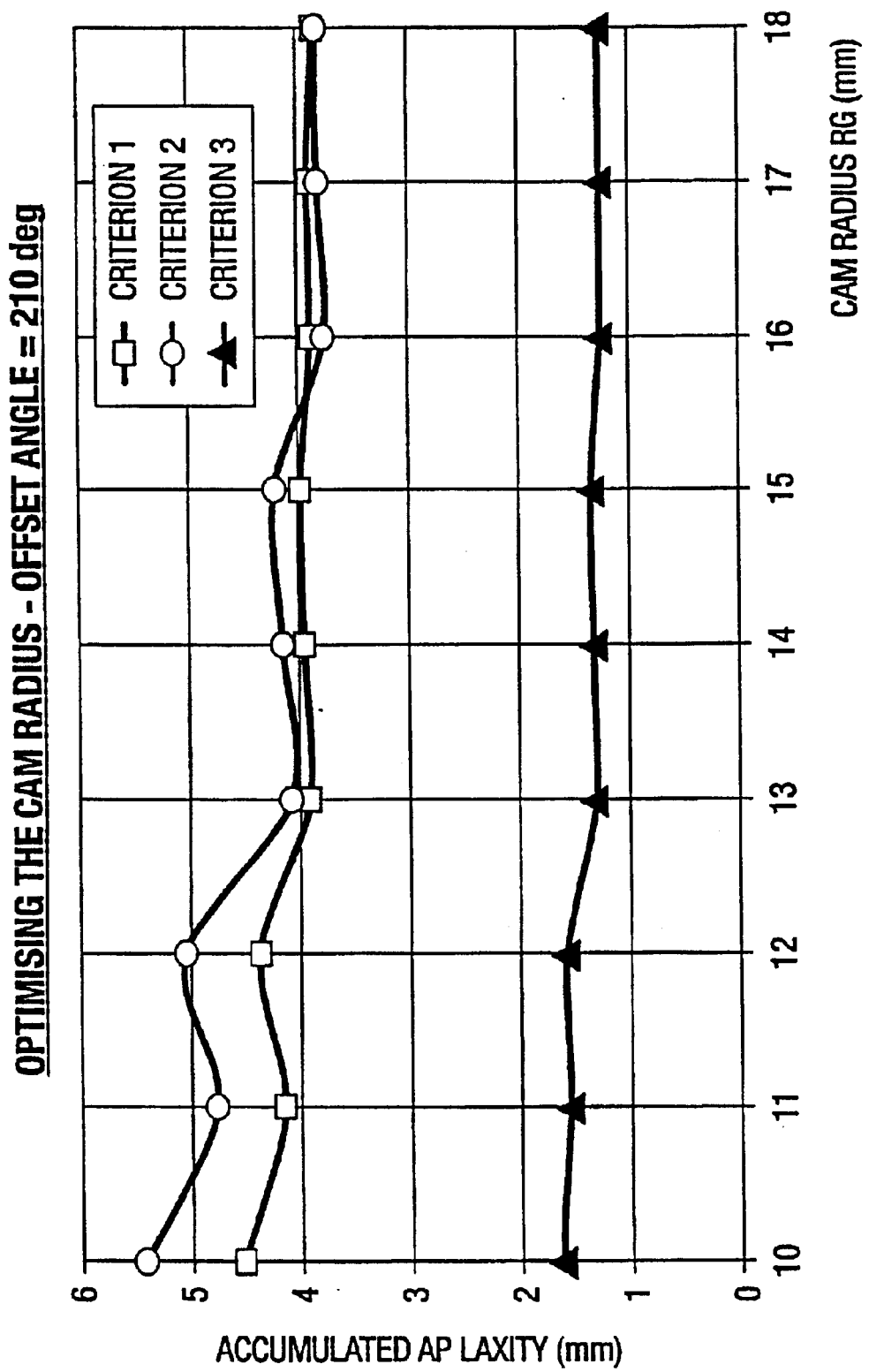
FIG. 6 shows graphically the accumulated anterior/posterior laxity at a variety of cam radii.
Figure 7:
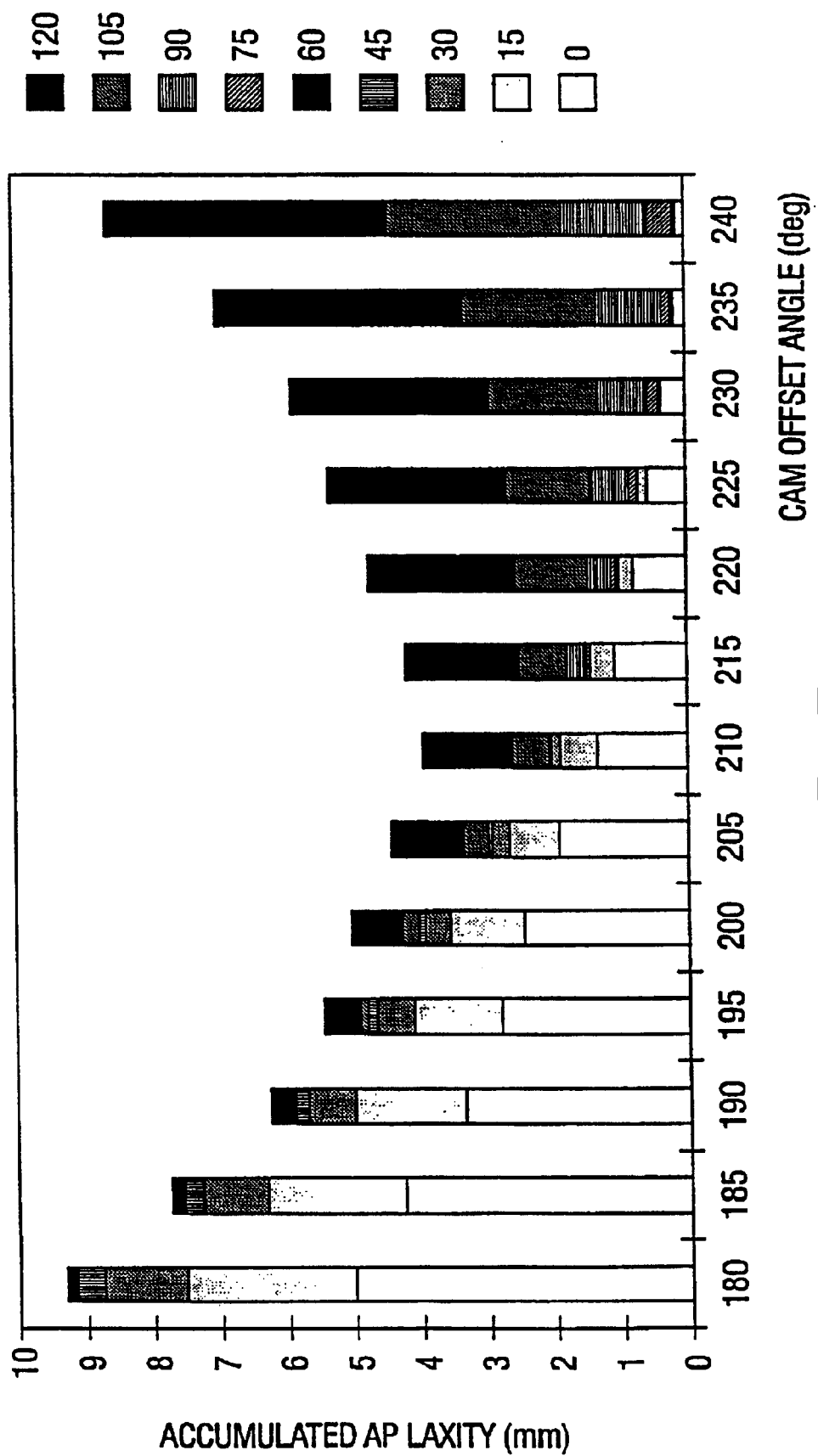
FIG. 7 shows graphically accumulated anterior/posterior laxity for different cam offset angles at different degrees of flexion.

For a TH of 210°, the variation of the laxity values for the three criteria, as a function of cam radius RG, are shown in FIG. 6. There was little difference between 13 mm and 18 mm, but below 13 mm there was an increase in laxity. FIG. 7 shows at which angles of flexion the largest laxities occurred, for a range of TH values. For TH less than the optimum of 210°, there were greater laxities at the smaller flexion angles; at TH values greater than 210° the opposite was the case. At a TH of 210°, the largest laxities occurred equally at the extremes of flexion, 0° and 120°.

It will thus be seen that for good control over posterior roll back, the centre of curvature of the TGS should lie posteriorly and downwardly from the major centre of curvature of the condylar surfaces, O. Typically, the cam offset angle may preferably be between about 190 and 230°.

Figure 8:
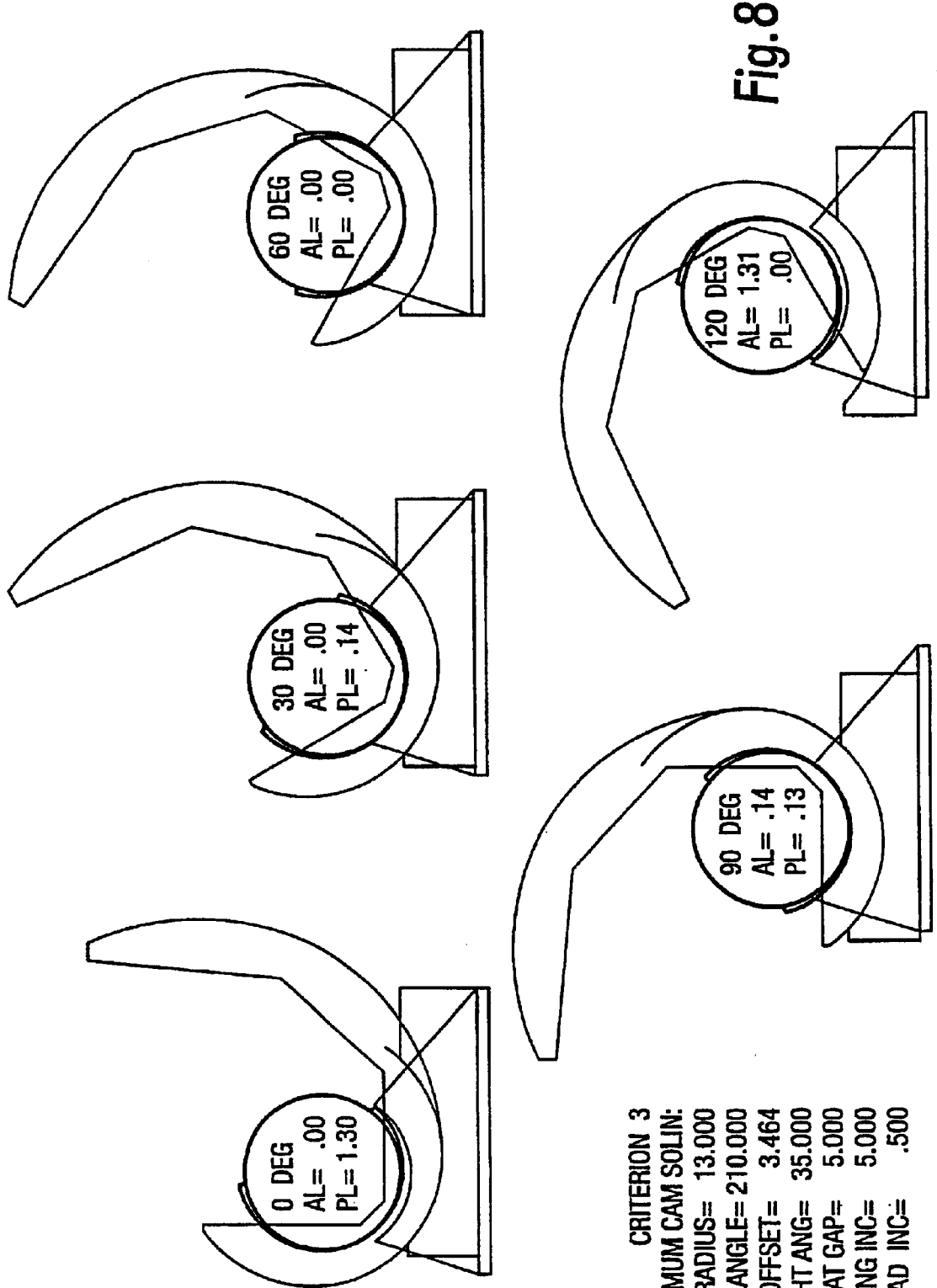
FIG. 8 illustrates the modification of the guide surfaces to reduce laxity.

The Femoral and Tibial Guide Surfaces (FGS, TGS) are shown for a cam with radius 13 mm offset at 210° in FIG. 8. Relative to the original circular shape of the FGS, it is seen that additional material has been added at 0° flexion and at 120° flexion, effectively increasing the peripheral radii of the cam. The small (1.3 mm) laxities can also be seen at 0° and 120° with negligible laxities in the mid-range of flexion.

In general, a posterior displacement of 10 to 20 mm will require a distance OP (see FIG. 1B) of about one half, e.g. 5 to 10 mm.

The preceding analysis is based on the simpler geometry of a femoral component in which the femoral condyles are circular when viewed sagitally. In practice, it is normally desirable to provide for maximum contact area at low degrees of flexion, e.g. 0- 15°, which interact during walking, the most frequent activity, while lower contact areas are permissible during climbing slopes or stairs, relatively infrequent activities. At the same time, posterior displacement of the femoral component will be low at small degrees of flexion, and will increase to a maximum at maximum flexion, e.g. from 100 - 130°. Anterior displacement may also be desirable in hyperextension of the prosthesis. Such variations in condylar radii are illustrated in FIG. 9. Also, the general pattern of the contact areas and points and their movement in posterior and anterior displacement is illustrated in FIG. 10.

The sagittal geometry of the femoral and tibial bearing surfaces can be specified in numerous ways. Certain geometries will be more suited to mobile bearing configurations, notably those with high femoral-tibial conformity, while reduced conformity is more suitable for fixed bearing or rotating platforms where anterior-posterior translation of the femur on the tibia is required. For the purposes of this analysis, the latter are specified (FIG. 9). The distal radius is continued posteriorly by 20 degrees, so that the same femoral-tibial conformity can by maintained during a walking cycle. In the mid-range of flexion the smaller radius contacts, while in high flexion, an even smaller radius comes into play in an effort to maximise the flexion angle of the knee.

A typical required sequence of femoral-tibial contact points as the knee flexes from 0 to 120 degrees is shown in FIG. 10. As the knee moves into extension from 15 degrees, there is a requirement to prevent further extension, which is provided by action of the hamstrings or gastrocnemius. To obtain efficiency of this action, an anterior contact point is required at 0 degree flexion. As the knee flexes, a contact point just posterior of the centre of the tibial bearing surface provides adequate lever arm for the quadriceps. Beyond 60 degrees, an increasingly posterior contact point further increases the quadriceps lever arm. Finally, beyond 105 degrees, a more rapid posterior translation of the contact point is an advantage for maximising the range of flexion. The sequence of contact points is represented generally, and the precise locations can vary by say 2–3 millimeters from those shown.

Given a typical sagital geometry for the femoral and tibial bearing surfaces, and the sequence of contact points, the rigid body motion of the femur can be determined geometrically. The method for synthesising the TGS for a given FGS has been described in mathematical terms above. The method can also be illustrated graphically (FIG. 11). The femur is positioned on the tibial bearing surface in the sequence of position shown in FIG. 10. The TGS needs to accommodate the multiple positions of the FGS. The TGS is then defined by the locus of the convex side of the multiple FGS positions. The anterior and posterior heights of the TGS are defined based on the required stability, or subluxation height. As described previously, the FGS can be subsequently modified by adding material at the anterior and posterior, which reduces the laxity at the extremes of motion. The resulting FGS and TGS still allow some laxity at the extremes, but overall, there is limitation of both anterior and posterior displacements, more especially in the mid-range of flexion.

Figure 12:
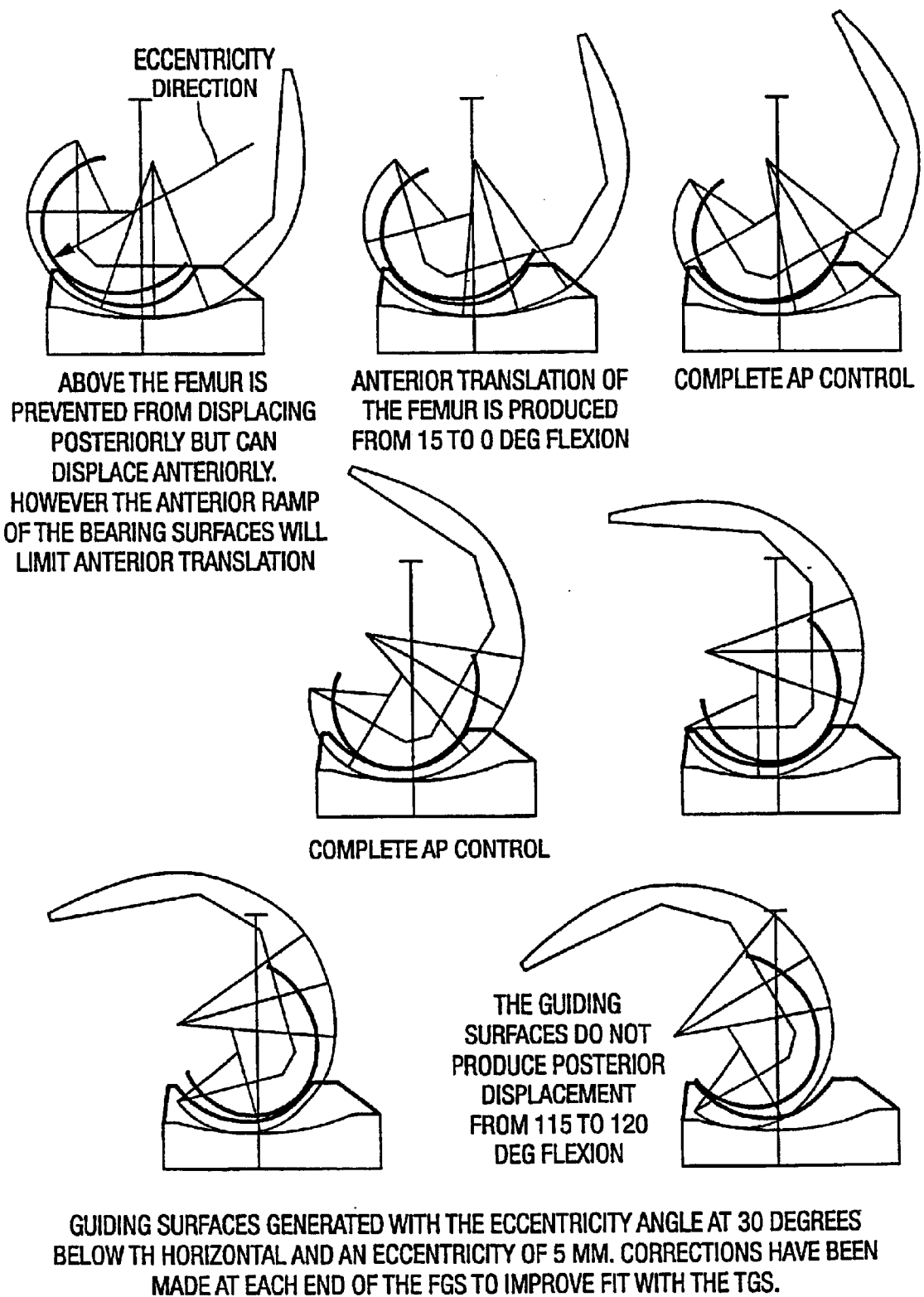
FIG. 12 illustrates control of flexion for an embodiment in which the cam offset angle is 210° and the eccentricity is 5 mm.

Using the method for generating the femoral and tibial guide surfaces described above, the configuration is shown which produces the least overall laxity, regardless of which criterion is used (FIG. 12). The FGS is convex and the TGS concave. With the knee in extensions, there is a small gap allowing the contact point to slide anteriority. In the mid-range of flexion there is complete control of anterior-posterior displacement up to 105 degrees. With this basic configuration of the FGS and TGS, a useful posterior translation of the contact points occur with flexion. However, at 120 degrees flexion, the Guide Surfaces do not produce the required posterior translations. This example illustrates the problem of obtaining guided motion throughout the entire flexion range.

To obtain more positive control in higher flexion, the eccentricity angle of the FGS can be set at 0 degree i.e. directed posteriorly, or even at 30 degrees above the horizontal (FIG. 13). A suitably large posterior displacement of the contact point can be achieved, while there is control in both the anterior and posterior directions. The posterior ramp of the TGS is shallower than ideal, but control of posterior displacement is not regarded as being quite so important because the contact is likely to roll and a slide down the slopes of the TGS and the posterior tibial bearing surface as the knee starts to extend form the fully flexed position. The combination of FGS and TGS shown in FIG.

13 is effective only after about 75° flexion. At lower flexion angles, anterior-posterior control is lost.

A variation of the above is achieved by reducing the radius and increasing the eccentricity of the FGS (FIG. 14). Here, after around 90 degrees flexion, a high posterior displacement can be achieved. The shapes resemble some posterior stablised designs. With an even smaller radius, the FGS and the TGS resemble yet other posterior stabilised designs.

At the opposite end of the flexion range, FGS and TGS surfaces can be produced which control the motion in early flexion, but not in late flexion (FIG. 15). This is achieved when the eccentricity angle is 90 degrees below the horizontal. Anterior-posterior control is lost after around 45 degrees of flexion. When the radius of the FGS is reduced and the eccentricity increased, anterior-posterior control can be achieved at low flexion (FIG. 16). The anterior displacement is higher, but control is lost at a lower flexion angle than the configuration of FIG. 15.

Typical embodiments in accordance with the invention are shown in FIGS. 1A, 1B, 17 and 18. In the case of FIG. 1A and 1B, a femoral component 1 comprises a pair of condylar surfaces 2 and 3, designed to have close conformity with plastic bearing components 4 and 5, which are arranged to slide on a tibial base plate 8. The femoral condyles 2 and 3 are bridged by a femoral guide surface 6, having a generally convex form when viewed sagitally as shown in FIG. 1B. Close conformity of the condylar surfaces with the dished areas of the bearing component (the plastic component) when viewed in transverse cross-section is also desirable.

A tibial guide surface 7 has anterior and posterior up-sweeps 9 and 10, which both provide the anterior and posterior guidance and also assist in stability by engaging within recesses such as 11 within the femoral component. In addition, the lateral surfaces of the tibial guide surface component engages with corresponding lateral surfaces internally of the condyles 2 and 3 to provide lateral stability.

Figure 17:
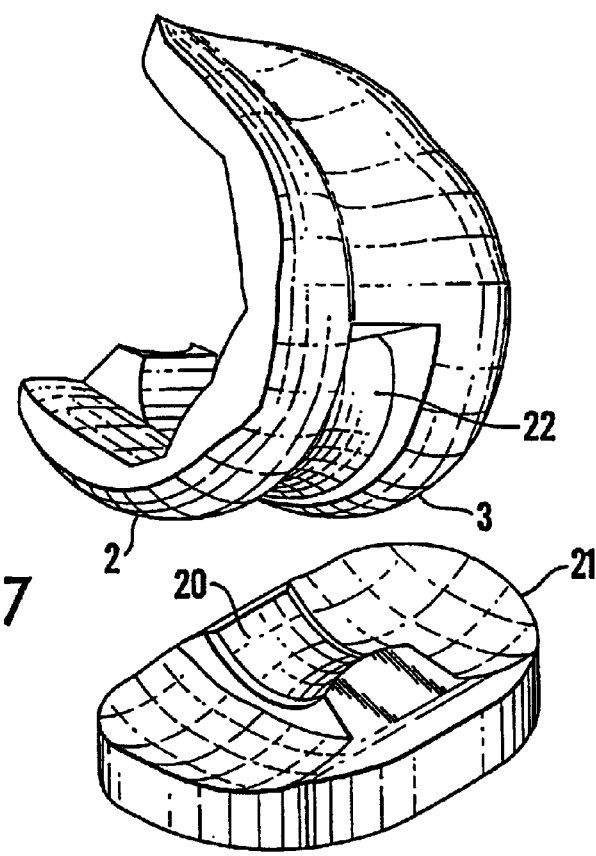
FIG. 17 is an exploded, perspective view of a further embodiment in which the TGS is integrally formed with the plastic bearing component.

FIG. 17 shows another embodiment in which the tibial guide surface 20 is formed as an integral part of the bearing component 21. Similarly, the femoral guide surface 22 may still be formed as an intercondylar surface but may be blended into the shape of the condyles 2 and 3. The latter may consist of conventionally shaped sagittal and frontal femoral profiles in contact with tibial bearing surfaces designed to be swept out by the femoral surfaces as they move through the maximum flexion range. In this embodiment, the tibial bearing surfaces need to allow for the anterior/posterior displacement, and the internal/external rotation. This could be achieved by making the tibial surfaces flat, thereby providing unrestricted rotational movement. Preferably, however, there should be some restraint and this can be achieved by making the tibial platform shallow at the centre, but upwardly curved at the anterior and posterior so as to limit the rotation to say ±12°. Alternatively, a sagittal radius can be provided in partial conformity with the femoral bearing surfaces to allow progressive restraint from the neutral position. In all these cases, the tibial guide surface will need to be modified to allow for the internal/external rotation. This can be achieved by generating a locus of the femoral guide surface as before, but including internal/external rotation at each flexion angle.

Figure 18:
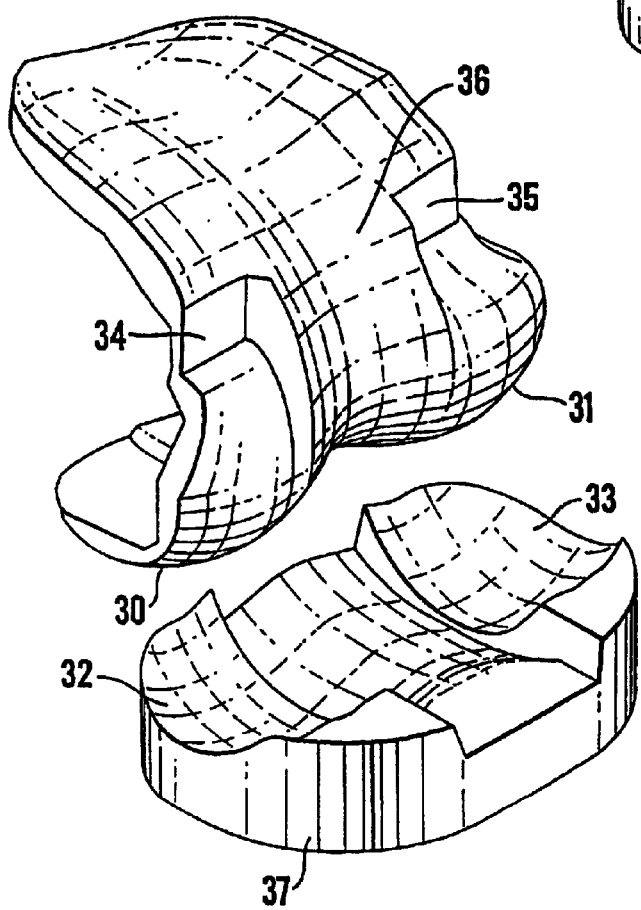
FIG. 18 is a view similar to FIG. 17 of a still further embodiment of a prosthesis in which the FGS and TGS surfaces are combined with the condylar, patella and tibial bearing surfaces.

Another possibility as illustrated in FIG. 18, is to provide for the condylar surfaces 30, 31 to also constitute the femoral guide surfaces. Similarly, the medial and lateral bearing surfaces 32, 33 of the tibial bearing component constitute the tibial guide surfaces.

To provide sufficient stability to prevent the femur subluxing forwards off the tibial surface, the anterior slope of the tibial guide surface must be sufficient to prevent this, as described by angle GC in FIG. 1B. This requires that the relatively small posterior femoral radius is carried forward anteriorly, producing lateral and medial notches 34, 35. These notches extend either side of the patella-bearing surface 36 which is shaped as for a standard condylar knee. In this embodiment, the bearing component 37 may be rotatable on a smooth tibial platform to provide for the internal/external rotational laxity.

It is, of course, possible to provide the method of generating guide surfaces for producing only posterior displacement with flexion or, alternatively, only anterior displacement with extension, although, preferably, there should be both anterior and posterior displacement. The appropriate choice can be made depending on the presence or absence of the anterior and posterior cruciate ligaments.

What is claimed is:

1. A condylar total knee replacement prosthesis which comprises:

(a) a femoral component adapted to be fixed to the femur and having a pair of femoral condylar surfaces;

(b) a tibial component adapted to be attached to the tibia and having a tibial platform; and (c) a mobile bearing component which is interposed between each condylar surface and the tibial platform and which has dished bearing surfaces adapted to support and conform with the corresponding femoral condylar surfaces, the mobile bearing component being slidable on the tibial platform in the anterior/posterior direction;

said femoral component having an intercondylar guide surface which is adapted to engage a corresponding tibial guide surface which is fixed on the tibial platform or is integral therewith, the intercondylar guide surface being rounded and having a center of curvature when viewed sagitally, which is offset from a major center curvature of the femoral condylar surfaces.

2. The prosthesis as claimed in claim 1, wherein the intercondylar guide surface has a radius of at least 10 mm.

3. The prosthesis as claimed in claim 1, wherein the posterior displacement is proportional to a degree of flexion of the prosthesis.

4. The prosthesis as claimed in claim 1, wherein the tibial guide surface has an anterior and posterior upward sweep, which engages in recesses in the femoral component to contribute to the stability of the prosthesis at or close to maximum flexion and extension.

5. The prosthesis as claimed in claim 1, wherein the tibial guide surface serves to control the anterior/posterior position of the femoral component relative to the tibial platform at any angle of flexion such that the total anterior/posterior laxity is less than 3 mm.

6. The prosthesis as claimed in claim 1, wherein the bearing components are mounted on the tibial platform so as to allow internal/external rotation.

7. The prosthesis as claimed in claim 1, in which the amount of posterior displacement of the femoral-tibial contact point is in the range of 6 to 16 mm.

8. The prosthesis as claimed in claim 1, wherein the femoral condylar surfaces are notched anteriorly to permit hyperextension while retaining conformity with the tibial bearing surfaces in a sagittal plane.

9. The prosthesis as claimed in claim 1, wherein the dished bearing surfaces closely conform with the corresponding femoral condylar surface.

* * * * *